United States Patent
Sharma et al.

(10) Patent No.: US 10,373,700 B2
(45) Date of Patent: *Aug. 6, 2019

(54) NON-INVASIVE FUNCTIONAL ASSESSMENT OF CORONARY ARTERY STENOSIS INCLUDING SIMULATION OF HYPEREMIA BY CHANGING RESTING MICROVASCULAR RESISTANCE

(71) Applicant: Siemens Healthcare GmbH, Erlangen (DE)

(72) Inventors: Puneet Sharma, Princeton Junction, NJ (US); Lucian Mihai Itu, Brasov (RO); Ali Kamen, Skillman, NJ (US); Bogdan Georgescu, Plainsboro, NJ (US); Xudong Zheng, Bangor, ME (US); Huseyin Tek, Princeton, NJ (US); Dorin Comaniciu, Princeton Junction, NJ (US); Dominik Bernhardt, Voerstetten (DE); Fernando Vega-Higuera, Erlangen (DE); Michael Scheuering, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/794,113

(22) Filed: Mar. 11, 2013

(65) Prior Publication Data
US 2013/0246034 A1    Sep. 19, 2013

Related U.S. Application Data

(60) Provisional application No. 61/610,134, filed on Mar. 13, 2012.

(51) Int. Cl.
| A61B 5/02 | (2006.01) |
| A61B 5/11 | (2006.01) |
| A61B 6/00 | (2006.01) |
| A61B 6/03 | (2006.01) |
| G16B 5/00 | (2019.01) |
| G16H 50/50 | (2018.01) |

(52) U.S. Cl.
CPC ............ *G16B 5/00* (2019.02); *A61B 5/02007* (2013.01); *A61B 5/1128* (2013.01); *A61B 6/032* (2013.01); *A61B 6/503* (2013.01); *A61B 6/5217* (2013.01); *G16H 50/50* (2018.01); *A61B 2576/023* (2013.01)

(58) Field of Classification Search
None
See application file for complete search history.

(56) References Cited

U.S. PATENT DOCUMENTS

| 7,953,266 B2 | 5/2011 | Gulsun et al. |
| 8,098,918 B2 | 1/2012 | Zheng et al. |
| 8,315,812 B2 | 11/2012 | Taylor |
| 8,386,188 B2 | 2/2013 | Taylor et al. |
| 2010/0067760 A1 | 3/2010 | Zhang et al. |
| 2011/0224542 A1 | 9/2011 | Mittal et al. |
| 2012/0022843 A1 | 1/2012 | Ionasec et al. |
| 2012/0041301 A1 | 2/2012 | Redel |
| 2012/0041735 A1* | 2/2012 | Taylor .............................. 703/9 |
| 2012/0072190 A1 | 3/2012 | Sharma et al. |
| 2012/0121151 A1 | 5/2012 | Bernhardt et al. |
| 2012/0203530 A1 | 8/2012 | Sharma et al. |
| 2014/0107935 A1* | 4/2014 | Taylor ............................ 702/19 |

OTHER PUBLICATIONS

Taylor, "Open Problems in Computational Vascular Biomechanics: Hemodynamics and Arterial Wall Mechanics," Comput Methods Appl Mech Eng, vol. 198, pp. 3514-3523, 2009.*
de Bruyne, "Simultaneous Coronary Pressure and Flow Velocity Measurements in Humans," Circulation, vol. 94, pp. 1842-1849, 1996.*
Anderson, "Coronary Artery Flow Velocity is Related to Lumen Area and Regional Left Ventricular Mass," Circulation, vol. 102, pp. 48-54, 2000.*
Chamuleau, "Association between coronary lesion severity and distal microvascular resistance in patients with coronary artery disease," Am J Physiol Heart Circ Physiol, vol. 285, pp. H2194-H2200, 2003.*
Bessems, "On the propagation of pressure and flow waves through the patient specific arterial system," doctoral dissertation, Technische Universiteit Eindhoven, Netherlands, 2007.*
Steele, "In Vivo Validation of a One-Dimensional Finite-Element Method for Predicting Blood Flow in Cardiovascular Bypass Grafts," IEEE Transactions on Biomedical Engineering, vol. 50(6), p. 649-656, 2004.*
Reichek, "Noninvasive determination of left ventricular end-systolic stress: validation of the method and initial application," Circulation, v 65(1), p. 99-108, 1982.*
Wieneke, "Determinants of coronary blood flow in humans: quantification by intracoronary Doppler and ultrasound," Journal of Applied Physiology, v 98(3), p. 1076-1082, 2005.*

(Continued)

*Primary Examiner* — G Steven Vanni

(57) ABSTRACT

A method and system for non-invasive assessment of coronary artery stenosis is disclosed. Patient-specific anatomical measurements of the coronary arteries are extracted from medical image data of a patient acquired during rest state. Patient-specific rest state boundary conditions of a model of coronary circulation representing the coronary arteries are calculated based on the patient-specific anatomical measurements and non-invasive clinical measurements of the patient at rest. Patient-specific rest state boundary conditions of the model of coronary circulation representing the coronary arteries are calculated based on the patient-specific anatomical measurements and non-invasive clinical measurements of the patient at rest. Hyperemic blood flow and pressure across at least one stenosis region of the coronary arteries are simulated using the model of coronary circulation and the patient-specific hyperemic boundary conditions. Fractional flow reserve (FFR) is calculated for the at least one stenosis region based on the simulated hyperemic blood flow and pressure.

21 Claims, 6 Drawing Sheets

(56) References Cited

OTHER PUBLICATIONS

"Open Problems in Computational Vascular Biomechanics: Hemodynamics and Arterial Wall Mechanics" C.A. Taylor et al. Comput Methods Appl Mech. Eng., vol. 198, pp. 3514-3523, 2009.
"Simultaneous Coronary Pressure and Flow Velocity Measurements in Humans" de Bruyne et al. Circulation, vol. 94, pp. 1842-1849, 1996.
"Coronary Atery Flow Velocity is Related to Lumen Area and Regional Left Ventricular Mass" H. Vernon Anderson et al. Circulation, vol. 102, pp. 48-54, 2000.
"Association Between Coronary Lesion Severity and Distal Microvascular Resistance in Patients With Coronary Artery Disease" Chamuleau et al. Am J Physiol Heart Circ Physiol, vol. 285, pp. H2194-H2200, 2003.

\* cited by examiner

300

310

320

330

NON-INVASIVE FUNCTIONAL ASSESSMENT OF CORONARY ARTERY STENOSIS INCLUDING SIMULATION OF HYPEREMIA BY CHANGING RESTING MICROVASCULAR RESISTANCE

This application claims the benefit of U.S. Provisional Application No. 61/610,134, filed Mar. 13, 2012, the disclosure of which is herein incorporated by reference.

BACKGROUND OF THE INVENTION

The present invention relates to non-invasive functional assessment of coronary artery stenosis, and more particularly, to non-invasive functional assessment of coronary artery stenosis from medical image data and blood flow simulations.

Cardiovascular disease (CVD) is the leading cause of deaths worldwide. Among various CVDs, coronary artery disease (CAD) accounts for nearly fifty percent of those deaths. Despite significant improvements in medical imaging and other diagnostic modalities, the increase in premature morbidity and mortality for CAD patients is still very high. The current clinical practice for diagnosis and management of coronary stenosis involves the assessment of the diseased vessel either visually or by Quantitative Coronary Angiography (QCA). Such assessment provides the clinician with an anatomical overview of the stenosis segment and parent vessel, including the area reduction, lesion length, and minimal lumen diameter, but does not provide a functional assessment of the effect of the lesion on blood flow through the vessel. Measuring the fractional flow reserve (FFR) by inserting a pressure wire into the stenosed vessel has been shown to be a better option for guiding revascularization decisions, since the FFR is more effective in identifying ischemia causing lesions, as compared to invasive angiography. QCA only evaluates the morphological significance if the stenosis and has a number of other limitations. Pressure wire based FFR measurements involve risks associated with the intervention necessary to insert the pressure wire into the vessel, and for a very narrow stenosis, the pressure wire may induce an additional pressure drop.

BRIEF SUMMARY OF THE INVENTION

The present invention provides a method and system for non-invasive functional assessment of coronary artery stenosis. Embodiments of the present invention provide a functional assessment of the severity of a coronary artery stenosis by calculating fractional flow reserve (FFR) and/or other functional measurements from medical image data and flow simulations. Embodiments of the present invention utilize an underlying reduced-order patient-specific hemodynamic analysis using computational fluid dynamics (CFD) simulations. This makes it possible to calculate FFR and other hemodynamic quantities characterizing the severity of a lesion in near real-time during the image acquisition process, thus allowing for an interactive workflow with a clinician. Embodiments of the present invention also utilize other non-image based non-invasive patient information to calculate boundary conditions for patient-specific CFD simulations.

In one embodiment of the present invention, patient-specific anatomical measurements of the coronary arteries are extracted from medical image data of a patient acquired during rest state. Patient-specific rest state boundary conditions of a model of coronary circulation representing the coronary arteries are calculated based on the patient-specific anatomical measurements and non-invasive clinical measurements of the patient at rest. Patient-specific hyperemic boundary conditions of the model of coronary circulation are calculated based on the rest boundary conditions and a model for simulated hyperemia. Hyperemic blood flow and pressure across at least one stenosis region of at least one coronary artery are simulated using the model of coronary circulation and the patient-specific hyperemic boundary conditions. Fractional flow reserve (FFR) of the at least one stenosis region is calculated based on the simulated hyperemic blood flow and pressure.

In another embodiment of the present invention, Patient-specific anatomical measurements of the coronary arteries from medical image data of a patient acquired during hyperemia state. Patient-specific hyperemic boundary conditions of a model of coronary circulation representing the coronary arteries are calculated based on the patient-specific anatomical measurements and non-invasive clinical measurements of the patient at hyperemia. Hyperemic blood flow and pressure across at least one stenosis region of at least one coronary artery are simulated using the model of coronary circulation and the patient-specific hyperemic boundary conditions. Fractional flow reserve (FFR) of the at least one stenosis region is calculated based on the simulated hyperemic blood flow and pressure.

These and other advantages of the invention will be apparent to those of ordinary skill in the art by reference to the following detailed description and the accompanying drawings.

DETAILED DESCRIPTION

The present invention relates to a method and system for non-invasive functional assessment of coronary artery stenosis using medical image data and blood flow simulations. Embodiments of the present invention are described herein to give a visual understanding of the methods for simulating blood flow and assessing coronary artery stenosis. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
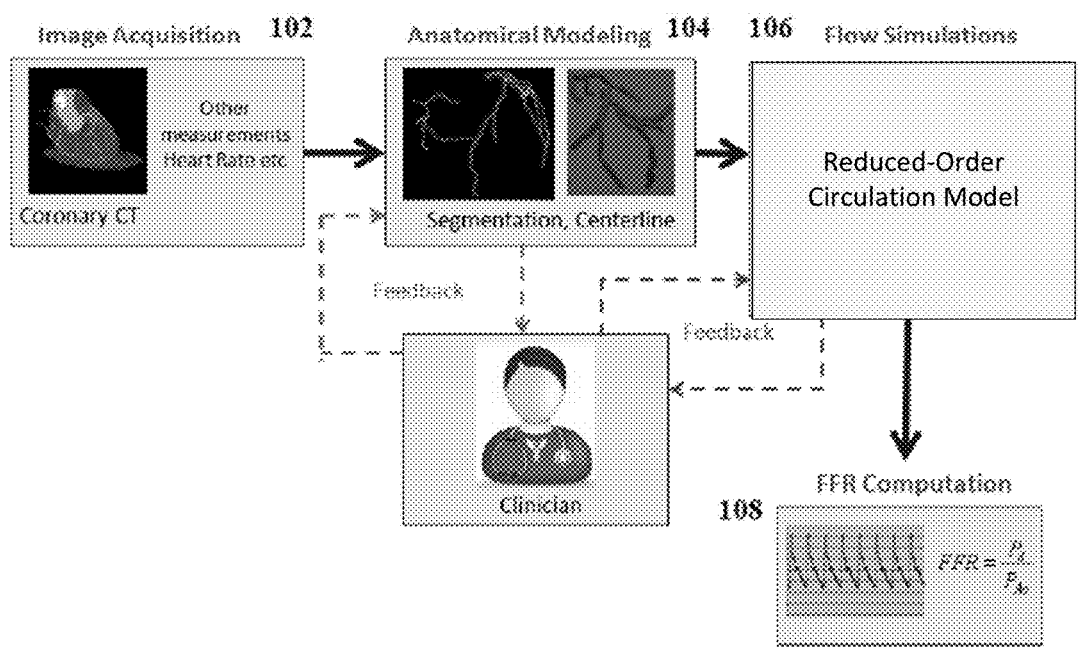
FIG. 1 illustrates a framework for non-invasive functional assessment of coronary artery stenosis according to an embodiment of the present invention.

FIG. 1 illustrates a framework for non-invasive functional assessment of coronary artery stenosis according to an embodiment of the present invention. As illustrates in FIG. 1, the framework includes an image acquisition stage 102, an anatomical modeling stage 104, a blood flow simulation stage 106, and a fraction flow reserve (FFR) computation phase 108. In the image acquisition stage 102, medical image data, such as coronary computed tomography (CT), of a patient is acquired, as well as other non-invasive clinical measurements, such as heart rate, blood pressure, etc. In the anatomical modeling stage 104, image segmentation and centerline extraction algorithms are used to generate patient-specific anatomical models of the patient's coronary arteries. The patient-specific anatomical models can be adjusted based on feedback from a clinician 110. In the blood flow simulation stage 106, computational fluid dynamics are used to simulate blood flow through the coronary arteries. In one embodiment, a reduced-order circulation model can be used for patient-specific blood-flow simulations in the vessel tree coupled with a separate model of each stenosis, and the underlying boundary conditions. Patient-specific boundary conditions are calculated using patient-specific modeling of maximal hyperemia conditions and the auto-regulation mechanism. The clinician 110 can provide feedback regarding the blood flow simulations, for example to change various parameters of the circulation model or to change the level of modeling of the circulation model. In the FFR computation stage 108, FFR is calculated for each stenosis based on the simulated pressures resulting from the blood flow simulation. The image acquisition stage 102, anatomical modeling stage 104, blood flow simulation stage 106, and FFR computation stage 108 are described in greater detail while referring to the method of FIG. 2

Figure 2:
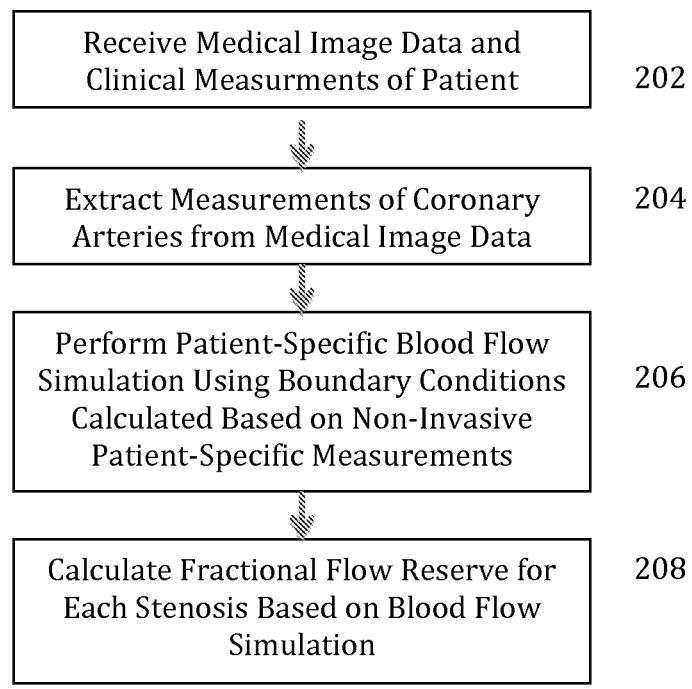
FIG. 2 illustrates a method for non-invasive functional assessment of coronary artery stenosis according to an embodiment of the present invention.

FIG. 2 illustrates a method for non-invasive functional assessment of coronary artery stenosis according to an embodiment of the present invention. Referring to FIG. 2, at step 202, medical image data and non-invasive clinical measurements of a patient is received. Medical image data from one or multiple imaging modalities can be received. For example, the medical image data can include, computed tomography (CT), Dyna CT, magnetic resonance (MR), Angiography, Ultrasound, Single Photon Emission computed Tomography (SPECT), and any other type of medical imaging modality. The medical image data can be 2D, 3D or 4D (3D+time) medical image data. The medical image data can be received directly from one or more image acquisition devices, such as a CT scanner, MR scanner, Angiography scanner, Ultrasound device, etc., or the medical image data may be received by loading previously stored medical image data for a patient.

In an advantageous embodiment, 3D coronary CT angiography (CTA) images are acquired on a CT scanner. The CTA images ensure that the coronary vasculature, including the vessel(s) that contain the stenosis, is adequately imaged using a contrast agent that is injected into the patient. At this stage, the clinician may be provided with an option of identifying lesions (stenoses) of interest by interactively viewing them on the images. This step can also be performed on the anatomical models that are extracted from the image data (step 204). Alternatively, the stenoses may be automatically detected in the image data using an algorithm for automatic detection of coronary artery stenosis, such as the method for automatic detection of coronary artery stenosis described in United States Published Patent Application No. 2011/0224542, which is incorporated herein by reference. In addition to the medical image data, other non-invasive clinical measurements, such as the patient's heart rate and systolic and diastolic blood pressure are also acquired.

Figure 3:
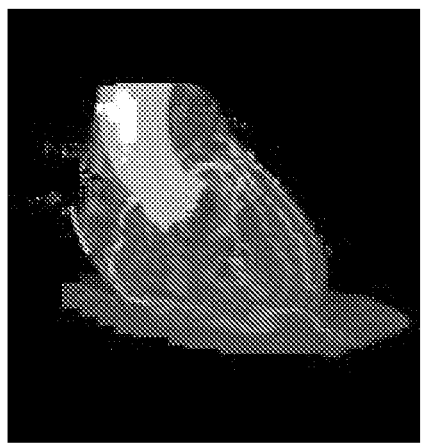
FIG. 3 illustrates exemplary results for generating a patient-specific anatomical model of the coronary vessel tree.
Figure 3:
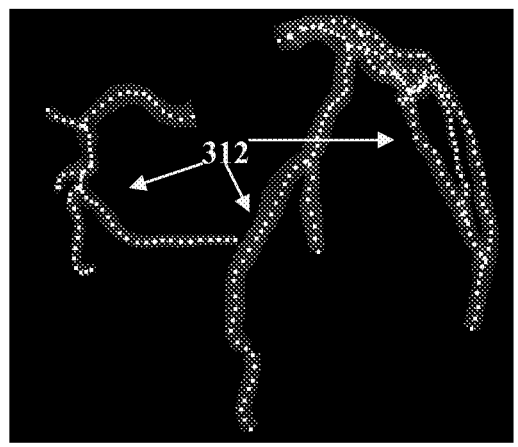
Figure 3:
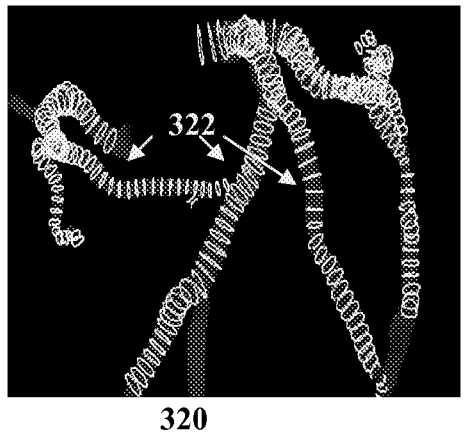
Figure 3:
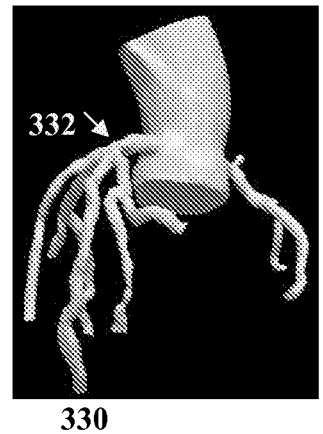

At step 204, measurements of the coronary arteries are extracted from the medical image data of the patient. In an exemplary embodiment, the medical image data is acquired at rest-state and the measurements of the coronary arteries are extracted from the image data acquired at rest-state. In an advantageous embodiment, the measurements of the coronary arteries are extracted by generating a patient-specific anatomical model of the coronary vessel tree is generated from the medical image data, but the present invention is not limited thereto. In order to generate the patient-specific anatomical model of the coronary arteries, the coronary arteries are segmented in the 3D medical image data using an automated coronary artery centerline extraction algorithm. The coronary arteries can be segmented using any coronary artery segmentation method. For example, the coronary arteries can be segmented in a CT volume using the method described United States Published Patent Application No. 2010/0067760, which is incorporated herein by reference. Once a coronary artery centerline tree is extracted, cross-section contours can be generated at each point of the centerline tree. The cross-section contour at each centerline point gives a corresponding cross-section area measurement at that point in the coronary artery. A geometric surface model is then generated for the segmented coronary arteries. For example, methods for anatomical modeling of the coronary arteries are described in U.S. Pat. Nos. 7,860,290 and 7,953,266, both of which are incorporated herein by reference. In addition to the coronaries, the patient-specific anatomical model can include the aortic root together with the proximal part of the aorta. A detailed 3D model of each stenosis is also extracted using similar algorithms, which includes the quantification of the proximal vessel diameter and area, distal vessel diameter and area, minimal lumen diameter and area, and length of stenosis. FIG. 3 illustrates exemplary results for generating a patient-specific anatomical model of the coronary vessel tree. Image 300 of FIG. 3 shows coronary CTA data. Image 310 shows a centerline tree 312 extracted from the CTA data. Image 320 shows a cross-section contours 322 extracted at each point of the centerline tree 312. Image 330 shows a 2D surface mesh 332 of the coronary arteries, the aortic root, and the proximal part of the aorta.

The above described anatomical modeling tasks can be performed automatically or can be user-driven, thereby allowing the user (clinician) to interactively make changes to the anatomical models to analyze the effects of such changes on the subsequent computation of FFR. In addition to the coronary vessel tree, the myocardium is also segmented (either automatically or manually) in the medical image data to determine an estimate of the left ventricular mass, which according to an embodiment of the present invention, is used to estimate the absolute resting flow for the patient. In an exemplary embodiment, a patient-specific anatomical model of the heart that is automatically generated from the image data. The anatomical heart model is a multi-component model having multiple cardiac components, including the four chambers (left ventricle, left atrium, right ventricle, and right atrium). The anatomical heart model may also include components such as the heart valves (aortic valve, mitral valve, tricuspid valve, and pulmonary valve) and the aorta. Such a comprehensive model of the heart is used to capture a large variety of morphological, functional, and pathological variations. A modular and hierarchical approach can be used to reduce anatomical complexity and facilitate an effective and flexible estimation of individual anatomies. The 4D anatomical heart model can be generated by generating individual models of each heart component, for example using marginal space learning (MSL), and then integrating the heart component models by establishing mesh point correspondence. Additional details regarding generation of such a 4D patient-specific heart model are described in United States Published Patent Application No. 2012/0022843, which is incorporated herein by reference Returning to FIG. 2, at step 206, a patient-specific blood flow simulation is performed using boundary conditions calculated based on non-invasive patient-specific clinical measurements. The hemodynamic quantities of interest for coronary circulation, such as FFR, are based on average values of flow or pressure over the cardiac cycle. For an efficient clinical workflow for evaluation of FFR via simulations, a balance between model complexity and computation time, without compromising on the accuracy of the results is desirable. In an advantageous embodiment of the present invention, reduced-order models are used for the patient-specific blood flow simulation, which enables the assessment of the functional significance of a coronary artery stenosis. The reduced-order models provide accurate estimates of flow and pressure distribution in the vessel tree, and are computationally efficient, thus enabling a seamless integration with the clinical workflow. Although the reduced order model is described herein for coronary circulation simulation, the present invention is not limited thereto, and a full-scale model or a multi-scale model can be used as well.

Figure 4:
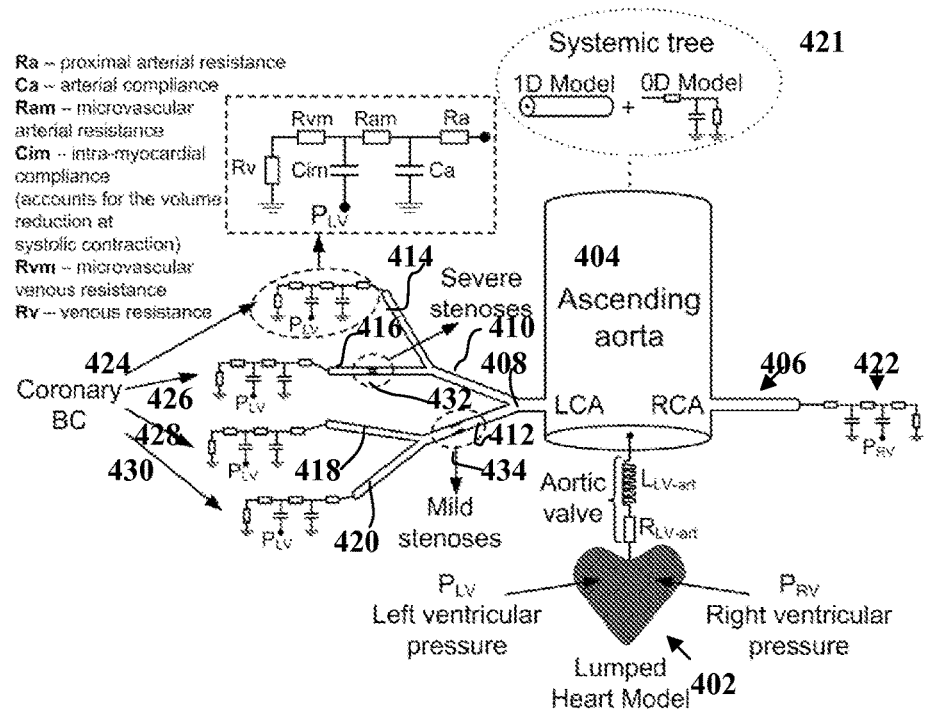
FIG. 4 illustrates a reduced-order model for simulating coronary circulation according to an embodiment of the present invention.

FIG. 4 illustrates a reduced-order model for simulating coronary circulation according to an embodiment of the present invention. As shown in FIG. 4, a heart model 402 is coupled at the root of the aorta. The heart model 402 may be implemented as a full 3D heart model or may be implemented as a lumped model parameterized through patient-specific data. The aorta and the large arteries (e.g., the left coronary artery (LCA), right coronary artery (RCA), etc.) are represented as 1D blood flow models 404, 406, 408, 410, 412, 414, 416, 418, and 420 since these 1D blood flow models 404-418 produce reliable results in terms of pressure and flow rate values and take into account wave propagation phenomena. All microvascular beds will be simulated through lumped parameter models 422, 424, 426, 428, and 430 which account for the resistance applied to the blood flow and for the compliance of the distal vessels. For the coronary arterial tree, the flow in the large (epicardial) vessels is computed through 1D models in a systemic tree model 421. The stenosis segments 432 and 434 (i.e., areas in the vessels were stenosis or narrowing is detected) cannot be simulated using the 1D blood flow models since there is a high variation in cross-sectional area and the shape of the stenosis influences the blood flow behavior and especially the trans-stenotic pressure drop which plays a major role in the assessment of the functional importance of such a stenosis. The coronary vascular bed is modeled through lumped parameter models 424, 426, 428, and 430, which are adapted to the coronary circulation in the sense that they take into account the effects of the myocardial contraction on the flow waveform.

Reduced-Order Model of Coronary Circulation

As shown in FIG. 4, the aorta (404), the large arteries supplied by the aorta (406, 408, 410, 412, 414, 416, 418, and 420), and the coronary epicardial vessels (421) are modeled as axi-symmetric 1-D vessel segments, where the blood-flow satisfies the following properties: conservation of mass, conservation of momentum, and a state equation for wall deformation. The vessel wall can modeled as a purely elastic or visco-elastic. The inlet boundary condition can be prescribed through an implicit coupling with the heart model 402, or through measured flow data. The outlet boundary condition is given by the implicit coupling with the models of the coronary vascular beds (424, 426, 428, and 430), while the junctions (bifurcations) are solved by considering the continuity of total pressure and flow. Additionally, the following loss coefficients may be introduced which account for the energy loss at the junctions, which depend on the angles between the vessel segments:

$$\frac{\partial A(t)}{\partial t} + \frac{\partial q(t)}{\partial x} = 0 \tag{1}$$

$$\frac{\partial q(t)}{\partial t} + \frac{\partial}{\partial t}\left(\alpha \frac{q^2(t)}{A(t)}\right) + \frac{A(t)}{\rho}\frac{\partial p(t)}{\partial x} = K_R \frac{q(t)}{A(t)} \tag{2}$$

$$p(t) = \frac{4}{3}\frac{Eh}{r_0}\left(1 - \sqrt{\frac{A_0}{A(t)}}\right), \tag{3}$$

where q is the flow rate, A is the cross-sectional area, p is the pressure, $\alpha$ is the momentum-flux correction coefficient, $K_R$ is a friction parameters, $\rho$ is the density, E is the Young modulus, h is the wall thickness and $r_0$ is the initial radius. The wall properties may be determined through an empirical relationship fit to the measured data in the extracted patient-specific anatomical model or based on patient-specific estimations of the wall compliance. Other alternative formulations of the quasi-1-D flow equations can also be used, modeling the effects of visco-elasticity, non-Newtonian behavior, etc.

Stenosis Model

The above quasi 1-D equations (Equations 1-3) are derived by considering a series of simplifying assumptions which all hold well for normal, healthy vessels. One of the assumptions is that the axial velocity is dominant and the radial components are negligible. This assumption no longer holds in case of sudden changes in lumen diameter, e.g. for a stenosis, and the radial components can no longer be excluded. Hence, the quasi 1-D equations do not correctly capture the pressure drop across the stenosis.

In terms of previous research activities, much attention has been directed towards the local velocity fields, but for the FFR assessment only the trans-stenotic pressure drop is important. In an advantageous implementation, semi-empirical stenosis models can be included in the 1-D blood flow models, which obtain accurate results as compared to full scale models. For example, in the model below, the pressure drop is expressed as a sum of three terms (viscous term, turbulent or Bernoulli term, and inertance term):

$$\Delta P_s = \frac{\mu K_v}{2\pi r_0^3}q + \frac{\rho K_t}{2A_0^2}\left(\frac{A_0}{A_s} - 1\right)^2|q|q + \frac{\rho K_u L_s}{A_0}\frac{\partial q}{\partial t}, \tag{4}$$

where $\mu$ is the blood viscosity, $L_s$ is the stenosis length, $K_v$, $K_t$ and $K_u$ are the viscous, turbulent, and inertance coefficients, respectively (all the quantities indexed with 0 refer to the normal dimensions while the quantities indexed with s refer to the stenosed values). In an advantageous embodiment, such a semi-empirical model for each stenosis segment (432 and 434) is coupled with the vessel tree (and the underlying heart and coronary bed models) to compute the physiological pressure drop across the stenosis, both during rest state and at maximal hyperemia. It is to be understood that the present invention is not limited to the semi-empirical stenosis model of Equation (4), and other such models of the stenosis, with multiple pressure drop factors, may be used alternatively. Additionally, in an alternative implementation, a full-order 3D model of each stenosis may be coupled with the rest of the vessel tree to simulate the pressure drop across the stenosis. In this case, the patient-specific 3D geometric model of the stenosis extracted from the medical image data (e.g., CTA data) is used in conjunction with quantitative coronary angiography (QCA)-like measures to personalize the stenosis model for the individual patient.

Regarding coupling of the reduced-order or full-order stenosis model to the rest of the coronary vessel tree, in a first possible implementation, the momentum equation is adapted and the additional pressure drop determined by the turbulent term is included on the right hand side of the equation as an additional loss term. In a second possible implementation, the regular momentum equation is disregarded completely and replaced by Equation (2). The segments treated as stenosis segments are coupled to the regular segments of the coronary vessel tree by considering continuity of total pressure and flow rate.

Patient-Specific Modeling of Coronary Bed Boundary Conditions

An important aspect of the flow simulations is represented by the boundary conditions at the termination of the coronary vessel tree (outflow boundary conditions). Generally, pressure, flow, or a relationship between flow and pressure may be imposed at the terminal sites of the arterial vessel tree. If measured data, e.g. time-varying velocity, flow rate, or even pressure, are available, they can be readily applied. In the absence of such information (which is typically the case), embodiments of the present invention calculate special boundary conditions that model the behavior of the distal arterial segments. Hence, the microvascular beds are modeled through lumped or O-D models: the systemic beds can represented by regular windkessel elements containing varying number of elements (for example, between two and four elements), while coronary beds are represented by special models which account for the influence of the myocardial contraction on the flow waveform (low during systole and high during early diastole). FIG. 4 displays an example of such specialized models for the coronary circulation and presents the detailed elements of this type of boundary condition.

The main characteristic of such lumped models is that the myocardial contraction is taken into account by introducing the left or right ventricular pressure, depending on the location of the coronary tree on the heart. The model displayed in FIG. 4 treats the microvascular bed as a single unit, but it is also possible to utilize more specialized models which consider separately the contribution of the subepicardial and subendocardial microvascular beds. Generally, subepicardial vessels are less affected by heart contraction (they represent the outer layers of the myocardium), while subendocardial vessels are more affected by the action of the outer (they represent the inner layers, closer to the heart chambers). This is the main reason why subendocardial are more prone to ischemia and to myocardial infarction.

Since the resistance values of the large vessels are very small compared to the resistances of the arterioles and capillaries, the overall pressure levels are almost solely determined by the microvascular beds. In the context of non-invasive FFR evaluation, the microvascular beds in general, and the coronary beds in particular play another major role. Since FFR is based on values determined at hyperemia, in order to non-invasively determine the value of this diagnostic indicator, the blood flow simulation has to model the hyperemic state. In clinical practice, FFR is measured after the intravenous or intracoronary administration of a vasodilator. In case of multi-vessel disease or serial stenosis it is important to have an increased duration of the hyperemic state in order to evaluate the functional significance of all stenosis and to generate reliable pull-back curves. Hence, often intravenous administration of the vasodilator is preferred. This leads to a slight increase of heart rate and decrease of blood pressure. Since for a simulation the effect of an intracoronary vasodilator can be extended indefinitely, and this alternative to obtain hyperemia does not influence heart rate and blood pressure, thus being easier to model, this approach is desirable. However, although the intravenous administration can be simulated, all microvascular beds have to be adapted accordingly.

The administration of hyperemia inducing drugs (adenosine, papaverine etc.) leads to a vasodilation effect of the microvascular beds, which represents an important decrease of the resistance values. The resistance values inside the systemic or coronary lumped models (for the normal state) may be obtained from patient-specific measurements, from literature data, or from the non-linear relationship between resistances and lumen size. Compliances play a secondary role since they only influence the transient values and not the average pressures which are of interest for the evaluation of FFR. The coronary hyperemic state is modeled through a corresponding decrease in the microvascular resistances, as caused by the administration of intracoronary adenosine (it has been shown that the epicardial, i.e. large arteries are not influenced by the vasodilator) and leads to a three to five-fold increase of normal coronary flow in healthy vessels. Coronary auto-regulation protects the myocardium against ischemia during rest state and leads to decreased resistances for the diseased vessel, the reference value being the flow which has to be identical to the noon-diseased case. The normal state can thus be easily modeled but does not represent a very high interest for the evaluation of FFR.

The main parameters which have to be estimated are the mean arterial pressure (MAP) and the coronary microvascular resistances (the resistances of the proximal epicardial arteries are negligible compared to the microvascular resistances). Since FFR uses only average measures of pressures (distal and proximal to the stenosis), compliances need not be estimated accurately because they only influence the waveform of pressure and flow, but not the average values, which are only determined by the resistances. MAP can be easily measured non-invasively and as stated previously is similar at both rest and hyperemia state. Coronary microvascular resistances on the other hand are much lower at hyperemia in order to allow for an increased flow rate. To determine the resistance values at hyperemia, first, the rest resistances can be estimated and then the effect of the administration of a vasodilation drug can be estimated and the hyperemia resistances can be estimated.

According to an advantageous embodiment of the present invention, the calculation of patient-specific boundary conditions for the coronary bed is implemented in two stages: in the first stage, the mean arterial pressure (MAP) and the coronary microvascular resistance at each outlet of the patient-specific vessel tree during a simulated rest-state are estimated, and in the second stage, the microvascular resistances at hyperemia are estimated.

Figure 5:
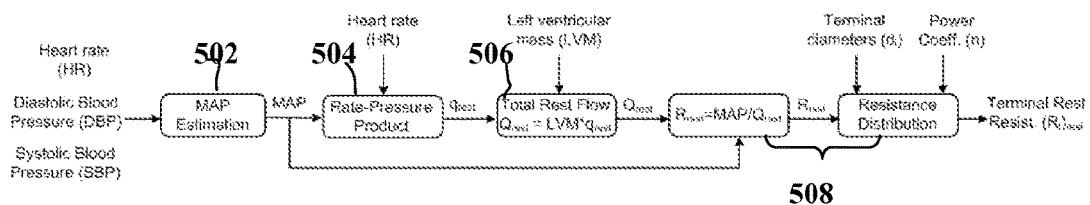
FIG. 5 illustrates a method for estimating rest-state microvascular resistance according to an embodiment of the present invention.

FIG. 5 illustrates a method for estimating rest-state microvascular resistance according to an embodiment of the present invention. As illustrates in FIG. 5, at step 502, mean arterial pressure (MAP) is estimated based on the patient's heart rate, systolic blood pressure, diastolic blood pressure. In particular, the MAP is calculated as $$\text{MAP} = \text{DBP} + [\tfrac{1}{3} + (\text{HR} \cdot 0.0012)] \cdot (\text{SBP} - \text{DBP}) \quad (5)$$

where HR, SBP, and DBP denote the patient's heart rate, systolic blood pressure, diastolic blood pressure, respectively, which are measure non-invasively.

At step 504, the total myocardial perfusion $q_{rest}$ is estimated using the rate-pressure product (RPP) relationship. The RPP is the product of the heart rate and the systolic blood pressure. Starting from the RPP, the resting perfusion $q_{rest}$ can be estimated as:

$$q_{rest} = 8 \cdot \{[0.7 \cdot (\text{HR} \cdot \text{SBP}) \cdot 10^{-3}] - 0.4\} \; [\text{ml/min}/100\,g], \quad (6)$$

where HR is the heart rate and SBP is the systolic blood pressure. It can be noted that this relationship is only valid if the flow meets the oxygen demand of the subject.

At step 506, the total resting coronary flow is estimated based on the resting perfusion $q_{rest}$ and the mass of the patient's left ventricle (LV). The mass of the left ventricle is estimated based on quantities derived from segmentation of the medical image data. In one possible implementation, the myocardium is segmented using automatic heart chamber segmentation, for example using a MSL machine-learning based method. The volume can be automatically calculated from the segmented myocardium, for example using the method described in U.S. Pat. No. 8,098,918, entitled "Method and System for Measuring Left Ventricle Volume", which is incorporated herein by reference. The LV volume is then multiplied by the density to provide the mass of the LV ($M_{LV}$).

In another possible implementation, the volume of the LV chamber can be determined as:

$$V = \frac{4}{3} \cdot \pi \cdot \frac{d_a}{2} \cdot \frac{d_l}{2} \cdot \frac{l}{2} \, [\text{ml}], \quad (7)$$

where $d_a$ and $d_l$ are two transverse diameters calculated from two perpendicular planes, and $l$ is the maximum chamber length measured on one of the perpendicular planes. The calculated volume is then corrected by a known regression equations:

$$V' = 0.928 \cdot V - 3.8 \, [\text{ml}]. \quad (8)$$

After measuring the wall thickness, the volume of the LV chamber together with the muscle wall can be calculated as follows:

$$V_{c+w} = \frac{4}{3} \cdot \pi \cdot \left(\frac{d_a}{2} + h\right) \cdot \left(\frac{d_l}{2} + h\right) \cdot \left(\frac{l}{2} + h\right) [\text{ml}]. \quad (9)$$

The LV mass can then be calculated as:

$$M_{LV} = (V_{c+w} - V') \cdot 1.050 \, [\text{kg}], \quad (10)$$

where 1.050 represents the specific gravity of the heart muscle.

In another possible implementation, the LV mass can be calculated as:

$$M_{LV} = 1.04 \cdot [(\text{LVEDD} + \text{IVSEDD} + \text{PWEDD})^3 - \text{LVEDD}^3] - 13.6, \quad (11)$$

where LVEDD is the left ventricular end-diastolic volume, IVSEDD is the intra-ventricular septum end-diastolic diameter, and PWEDD is the posterior wall end-diastolic diameter.

In order to determine the absolute value of the resting flow, the resting perfusion has to be multiplied by the myocardial mass. In normal hearts, it is generally assumed that the left ventricle represents two thirds of the total mass, while the right ventricle and atria represent the other third. Accordingly, once the left ventricular mass $M_{LV}$ is determined, the absolute resting flow can be determined as:

$$Q_{rest} = q_{rest} \cdot 1.5 \cdot M_{LV} \, [\text{ml/min}]. \quad (12)$$

Having determined that the flow rate is proportional to the cube of the radius, absolute resting flow, which is the sum of all outflow flows of the coronary vessels may be expressed as:

$$Q_{rest} = \sum_{i=1}^{n} k \cdot r_i^3 = \sum_{i=1}^{n} Q_i. \quad (13)$$

At step 508, the terminal resistance for each vessel is calculated. In particular, the terminal resistance is calculated using the following relationship:

$$R_i = \frac{\text{MAP}}{Q_i}. \quad (14)$$

$Q_i$ is determined by:

$$\frac{Q_i}{Q_{rest}} = \frac{k \cdot r_i^3}{\sum_{j=1}^{n} k \cdot r_j^3} = \frac{r_i^3}{\sum_{j=1}^{n} r_j^3}, \quad (15)$$

and hence:

$$Q_i = \frac{Q_{rest} \cdot r_i^3}{\sum_{j=1}^{n} r_j^3}, \quad (16)$$

where $r_i$ is the terminal radius of a vessel (equal to half of the terminal diameter $d_i$) and n is a power coefficient. Thus, the terminal resistance at each vessel can be calculated as:

$$R_i = \frac{\text{MAP}}{Q_i} = \frac{\text{MAP} \cdot \sum_{j=1}^{n} r_j^3}{Q_{rest} \cdot r_i^3}. \quad (17)$$

The second stage of estimating the patient-specific coronary bed boundary conditions calculates hyperemic-state microvascular resistances. The input to the second stage is represented by the rest microvascular resistances calculated using Equations (5)-(17), as described in the method of FIG. 5. The coronary hyperemic state can be modeled by decreasing the microvascular resistances, which is caused by the administration of intracoronary adenosine. It has been shown that the epicardial arteries are not influenced by the vasodilator, thus only the microvascular resistance needs to be changed. This ultimately leads to a three to five-fold increase of coronary flow in healthy vessels. Adenosine leads to an increase in coronary flow velocity of around 4.5 for normal, healthy subjects (with no coronary artery disease). The coronary flow velocity reserve (CFVR) value is determined after the administration of intracoronary boluses, intracoronary infusions, or intravenous infusions to a series of subjects. The value of 4.5 is confirmed in all three sets of experiments. The increase in coronary velocity is equal to an increase in flow, since a similar velocity profile can be assumed for both rest and hyperemic state. Since during hyperemia, blood pressure decreases slightly, a 4.5-fold increase in flow does not mean a 4.5-fold decrease in coronary resistance. A total coronary resistance index (TCRI) can be computed as described below.

The hyperemic microvascular resistances can be calculated as follows. First, the resting average peak velocity is calculated based on the patient's heart rate and systolic blood pressure as:

$$rAPV=0.0009 \cdot SBP \cdot HR+5.925 \text{ [cm/s]}, \tag{18}$$

where the rate-pressure product is expressed in [mmHg*beats/min]. CFVR values can then be calculated for each mean branch of the coronary vessel tree using the following equations:

$$\text{LAD: CFVR}=10^{1.16-0.48 \cdot \log(rAPV)-0.0025 \cdot age} \tag{19}$$

$$\text{LCX: CFVR}=10^{1.14-0.45 \cdot \log(rAPV)-0.0031 \cdot age} \tag{20}$$

$$\text{RCA: CFVR}=10^{1.15-0.50 \cdot \log(rAPV)-0.0021 \cdot age}. \tag{21}$$

The TCRI can then be calculated using a value of 5 mmHg for $\Delta MAP$:

$$\frac{1}{TCRI} = \frac{\frac{MAP_{rest}}{Q_{rest}}}{\frac{MAP_{hyper}}{Q_{hyper}}} = \frac{MAP_{rest}}{MAP_{hyper}} \cdot \frac{Q_{hyper}}{Q_{rest}} = \tag{22}$$

$$\frac{MAP_{rest}}{MAP_{hyper}} \cdot CFVR = \frac{MAP_{rest}}{MAP_{rest} - \Delta MAP} \cdot CFVR.$$

Alternatively, instead of the above described steps, the following relationship may be used to determine the TCRI value, based on experimental results having a very low standard deviation and thus high reliability:

$$TCRI = \begin{cases} 0.0016 \cdot HR + 0.1 & \text{for } HR \leq 100 \text{ bpm} \\ 0.001 \cdot HR + 0.16 & \text{for } HR > 100 \text{ bpm}. \end{cases} \tag{23}$$

Figure 6:
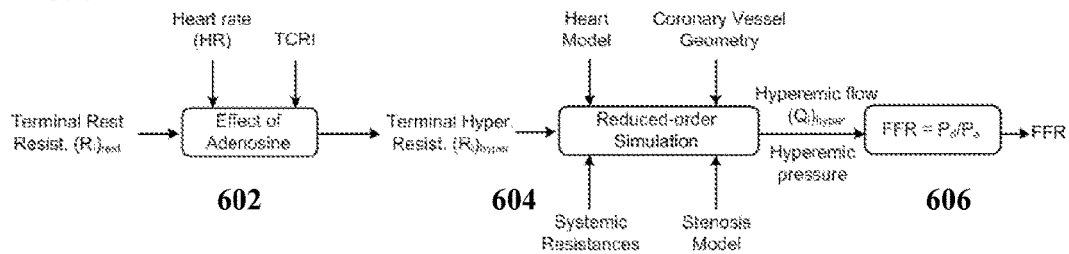
FIG. 6 illustrates the calculation of FFR using a personalized reduced order model according to an embodiment of the present invention.

The hyperemic microvascular resistances are then calculated based on the resting-state microvascular resistances, using the following equation:

$$(R_i)_{hyper}=(R_i)_{rest} \cdot TCRI, \tag{24}$$

where $(R_i)_{rest}$ is the value for the resting-state microvascular resistance determined using the method of FIG. 6, described above. It is to be understood that alternative methods for estimating the microvascular resistance at hyperemia can also be readily incorporated into the method for calculating FFR described herein.

Heart Model

The intra-myocardial pressure is an important element of the coronary modeling. Hence, a major component of the reduced-order modeling is the heart model. FIG. 4 displays a lumped heart model 402 but also more sophisticated or complete models may be used. There are several lumped models, such as the varying elastance model and the single fiber model. These can determine the pressure and the flow in the different heart chambers without considering a spatial model of the heart. Several parameters like contractility, stroke volume, time-to-maximum, dead volume ($V_0$), heart rate can be adapted in order to account for different states of the body and to personalize the model. The simplest model is represented by the varying elastance model which can readily be coupled to the aortic input through a lumped aortic valve model 402 and indirectly coupled to the specialized microvascular models of the coronary arterial tree through the left ventricular pressure. The varying elastance model can be expressed as:

$$E(t) = \frac{P_{LV}(t)}{V_{LV}(t) - V_0}. \tag{25}$$

Several considerations have lead to the modeling of all major arteries of the systemic tree and not only of the coronary arterial tree. This way the heart can be directly coupled to the aorta and the flow is determined by the interaction between the left ventricle and the system impedance. Also, the overall pressure level is mainly determined by the large arteries, while the coronary resistances (microvascular and stenosis-based) have a negligible influence and hence the trans-stenotic pressure drops may be modeled more precisely. Depending on the additional data available (such as echocardiography, Cardiac MRI), the heart models can be further personalized for an individual patient. These modalities allow for information such as stroke volume, ejection fraction etc, which can readily be used to personalize the heart model.

Returning to FIG. 2, at step 208, FFR is calculated for each stenosis based on the blood flow simulations. Once the time-varying pressure and flow rates are computed from the patient-specific reduced-order simulations at maximal vasodilation, the FFR value is determined by simply taking the ratio of the mean pressure distal to the stenosis ($P_d$) with respect to the mean aortic pressure ($P_a$) during the cardiac cycle:

$$FFR = \frac{P_d}{P_a}. \tag{26}$$

This calculation can be performed automatically for all the lesions that the user specified during the anatomic modeling step. Additionally, the user can also specify any location in the vessel tree during a post-processing step, and the corresponding FFR value will then be computed as described above.

FIG. 6 illustrates the calculation of FFR using a personalized reduced order model according to an embodiment of the present invention. As shown in FIG. 6, at 602, the effect of the adrenosine on the terminal resting-state microvascular resistances is estimated, resulting in the terminal hyperemia microvascular resistances. At 604, the reduce order simulation is performed using the heart model, coronary vessel geometry, estimates resistances at hyperemia, and the stenosis model. The simulation simulates the hyperemic blood flow and hyperemic pressure. At 606, FFR is calculated as a ratio of the simulated mean hyperemic pressure distal to the stenosis ($P_d$) and the mean hyperemic aortic pressure ($P_a$) over a cardiac cycle. In addition to FFR, other hemodynamic quantities based on the flow rates and pressure can also be calculated from the results of the blood flow simulations.

In addition to Coronary CT data, the above method can also be applied on other image data, such as 3-D Angio, Rotational Angiography, Dyna-CT. For angiographic data, the image based analysis of the propagation of the contrast agent, via a spatio-temporal representation of contrast propagation can be used to robustly recover the flow rate over time, both during resting and maximal hyperemia. At the same time, such image acquisition can also be carried out during maximal hyperemia condition, and used in conjunction with the empirical stenosis model to determine the FFR value. Accordingly, in an alternative embodiment of the present invention, the medical image data can be acquired at hyperemia, and the hyperemia boundary conditions detected directly based on the image data and non-invasive non-imaging measures (e.g., heart rate, systolic blood pressure, and diastolic blood pressure) acquired at hyperemia. The simulations using the hyperemia boundary conditions can then be used to calculate FFR.

Other sources of patient information (when present) can be used for further personalization of the models. For example, echocardiography can provide 3-D strain maps, which may be used to model the influence of the heart contractions on each of the epicardial coronary vessels. There is a major difference between the right and left side of the heart but also locally more detailed variations can be taken into account. A 3-D strain map extracted from the image data may be used for imposing additional patient-specific boundary conditions. Along the same lines, 3-D color flow or Phase Contrast MRI measurements can also be used to provide inlet flow boundary conditions for the coronary vessel tree. The availability of 3-D+t anatomical models of the heart (from CT, MR or Ultrasound data) makes it possible to simulate the blood flow in the heart chambers by CFD. This can also be used to further personalize the models and impose the boundary conditions.

Since the FFR values are computed in near real-time using the reduced-order simulation model, a clinician can provide feedback to observe the effects of various changes, such as variability due to changes in the segmentation result, variability due to changes in the seed point for centerline extraction and missing centerlines, variability due to changes in locations of branch terminations and the effect on the boundary conditions, variability due to side vessel branch elimination, and variability due to overall image quality.

Instead of using the rate-pressure product in order to determine coronary perfusion, as described above, in an alternative implementation it is possible to use the stress-mass-rate product in order to determine directly the global coronary flow:

$$\text{Stress} = \frac{0.334 \cdot SBP \cdot LVDd}{LVPWT} \cdot \left(1 + \frac{LVPWT}{LVDd}\right) \quad (27)$$

where SBP is systolic blood pressure, LVDd is left ventricle diameter at end-diastole and LVPWT is left ventricular posterior wall thickness. The global coronary resting flow can then be determined as follows:

$$Q_{rest} = 0.0218 \cdot \text{Stress} \cdot M_{LV} \cdot HR \cdot 10^{-3} + 120.11, \quad (28)$$

where the stress-mass-rate product is expressed in [g*kdyne/cm2*beats/min] and MLV represents the left ventricular mass.

Figure 7:
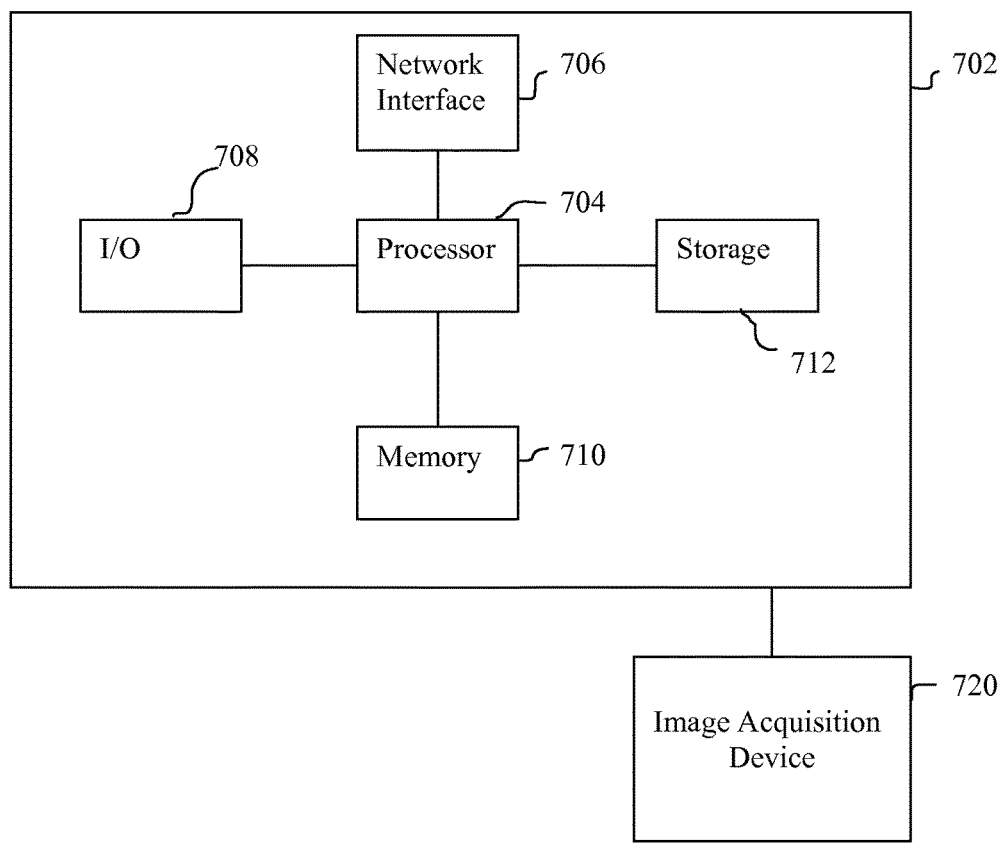
FIG. 7 is a high-level block diagram of a computer capable of implementing the present invention.

The above-described methods for non-invasive assessment of coronary artery stenosis may be implemented on a computer using well-known computer processors, memory units, storage devices, computer software, and other components. A high-level block diagram of such a computer is illustrated in FIG. 7. Computer 702 contains a processor 704, which controls the overall operation of the computer 702 by executing computer program instructions which define such operation. The computer program instructions may be stored in a storage device 712 (e.g., magnetic disk) and loaded into memory 710 when execution of the computer program instructions is desired. Thus, the steps of the methods of FIG. 2 may be defined by the computer program instructions stored in the memory 710 and/or storage 712 and controlled by the processor 704 executing the computer program instructions. An image acquisition device 720, such as a CT scanning device, MR scanning device, Ultrasound device, etc., can be connected to the computer 702 to input image data to the computer 702. It is possible to implement the image acquisition device 720 and the computer 702 as one device. It is also possible that the image acquisition device 720 and the computer 702 communicate wirelessly through a network. The computer 702 also includes one or more network interfaces 706 for communicating with other devices via a network. The computer 702 also includes other input/output devices 708 that enable user interaction with the computer 702 (e.g., display, keyboard, mouse, speakers, buttons, etc.). Such input/output devices 708 may be used in conjunction with a set of computer programs as an annotation tool to annotate volumes received from the image acquisition device 720. One skilled in the art will recognize that an implementation of an actual computer could contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for non-invasive assessment of coronary artery stenosis, comprising:
   extracting patient-specific anatomical measurements of the coronary arteries from medical image data of a patient acquired during a rest state;
   automatically detecting at least one stenosis region in at least one coronary artery from the medical image data;
   calculating by a processor patient-specific rest state boundary conditions of a model of coronary circulation representing the coronary arteries using the patient-specific anatomical measurements and non-invasive clinical measurements of the patient at rest, wherein calculating the patient-specific rest state boundary conditions comprises calculating a resting microvascular resistance at a termination of each of a plurality of branches of the coronary arteries using the patient-specific anatomical measurements and the non-invasive clinical measurements of the patient at rest;

calculating by a processor patient-specific hyperemic boundary conditions of the model of coronary circulation using the rest boundary conditions and a model for simulated hyperemia, wherein the model for simulated hyperemia simulates hyperemia in the patient by changing only the resting microvascular resistance at a termination of each of a plurality of branches of the coronary arteries to a hyperemic microvascular resistance calculated as a function of the resting microvascular resistance at the termination of each of the plurality of branches without changing blood pressure or heart rate boundary conditions, and wherein calculating the patient-specific hyperemic boundary conditions comprises calculating the hyperemic microvascular resistance at the termination of each of the plurality of branches using the calculated resting microvascular resistance by:

calculating a resting average peak velocity as a function of a measured heart rate and a measured systolic blood pressure of the patient, calculating a coronary flow velocity reserve (CFVR) value for each branch of the coronary arteries as a function of the resting average peak velocity and an age of the patient, calculating a patient-specific total coronary resistance index (TCRI) as a function of the CFVR value and an estimated resting mean arterial pressure (MAP), and calculating the hyperemic microvascular resistance at the termination of each of the plurality of branches as a function of the calculated resting microvascular resistance and the patient-specific TCRI;

simulating by a processor hyperemic blood flow and pressure across the at least one automatically detected stenosis region of the at least one coronary artery using the model of coronary circulation and the patient-specific hyperemic boundary conditions, wherein the model of coronary circulation comprises a reduced order stenosis pressure drop model representing the at least one stenosis region and the reduced order stenosis pressure drop model calculates a pressure drop across the at least one stenosis region as a sum of a viscous term, a turbulent term, and an inertance term:

$$\Delta P_s = \frac{\mu K_v}{2\pi r_0^3}q + \frac{\rho K_t}{2A_0^2}\left(\frac{A_0}{A_s}-1\right)^2|q|q + \frac{\rho K_u L_s}{A_0}\frac{\partial q}{\partial t},$$

where $\mu$ is blood viscosity, $L_s$ is a length of the at least one stenosis region, $q$ is a flow rate, $A_s$ is a cross-sectional area of the at least one stenosis region, $A_0$ is a cross-sectional area of a non-stenosis region in the at least one coronary artery, $\rho$ is a blood density, $r_0$ is a radius of the non-stenosis region in the at least one coronary artery, and $K_v$, $K_t$ and $K_u$ are viscous, turbulent, and inertance coefficients, respectively; and calculating by a processor fractional flow reserve (FFR) of the at least one stenosis region using the simulated hyperemic blood flow and pressure.

2. The method of claim 1, wherein the coronary circulation model comprises one-dimensional computational models representing the coronary arteries and aorta of the patient.

3. The method of claim 2, wherein the reduced order stenosis pressure drop model representing the at least one stenosis region is coupled to the one-dimensional computational model representing the at least one coronary artery.

4. The method of claim 3, wherein the reduced order stenosis pressure drop model representing the at least one stenosis region is coupled to the one-dimensional computational model representing the at least one coronary artery using a momentum equation that includes a pressure drop determined by the turbulent term as a loss term.

5. The method of claim 1, wherein calculating the resting microvascular resistance at the termination of each of the plurality of branches using the patient-specific anatomical measurements and the non-invasive clinical measurements of the patient at rest comprises:

calculating the mean arterial pressure (MAP) as a function of the measured heart rate, the measured systolic blood pressure, and a measured diastolic blood pressure of the patient;

calculating a total resting coronary flow as a function of a product of an estimated stress value, a mass of a left ventricle of the patient, and the measured heart rate; and calculating the resting microvascular resistance at the termination of each of the plurality of branches as a function of the MAP and the total resting coronary flow.

6. The method of claim 5, wherein calculating a total resting coronary flow as a function of a product of an estimated stress value, a mass of a left ventricle of the patient, and the measured heart rate comprises:

calculating the estimated stress value as a function of the measured systolic blood pressure, a diameter of the left ventricle of the patient at end-diastole, and a posterior wall thickness of the left ventricle.

7. The method of claim 5, wherein calculating a total resting coronary flow as a function of a product of an estimated stress value, a mass of a left ventricle of the patient, and the measured heart rate comprises:

calculating the estimated stress value as $$\text{Stress} = \frac{0.334 \cdot SBP \cdot LVDd}{LVPWT}\cdot\left(1+\frac{LVPWT}{LVDd}\right),$$

where SBP is the measured systolic blood pressure, LVDd is a diameter of the left ventricle of the patient at end-diastole, and LVPWT is a posterior wall thickness of the left ventricle of the patient; and calculating the total resting coronary flow as $$Q_{rest}=0.0218\cdot\text{Stress}\cdot M_{LV}\cdot HR\cdot 10^{-3}+120.11,$$

where $M_{LV}$ is the mass of the left ventricle of the patient and HR is the measured heart rate.

8. The method of claim 1, wherein calculating a resting average peak velocity as a function of a measured heart rate and a measured systolic blood pressure of the patient comprises:

calculating the resting average peak velocity as $rAPV=0.0009\cdot SBP\cdot HR+5.925$ where SBP is the measure systolic blood pressure and HR is the measure heart rate.

9. The method of claim 1, wherein calculating a patient-specific total coronary resistance index (TCRI) as a function of the CFVR value and an estimated resting mean arterial pressure (MAP) comprises:

calculating the patient-specific $$TCRI \text{ as } \frac{1}{TCRI} = \frac{MAP_{rest}}{MAP_{rest} - \Delta MAP}.$$

CFVR, wherein $MAP_{rest}$ is the estimated resting mean MAP and $\Delta MAP$ is a predetermined constant value.

10. The method of claim 1, wherein calculating the hyperemic microvascular resistance at the termination of each of the plurality of branches as a function of the calculated resting microvascular resistance and the patient-specific TCRI comprises:
   calculating the hyperemic microvascular resistance at the termination of each of the plurality of branches as a product of the calculated resting microvascular resistance and the patient-specific TCRI.

11. The method of claim 2, wherein the coronary circulation model further comprises lumped models representing coronary microvascular beds, each coupled to a termination of a one-dimensional computational model representing a coronary artery branch.

12. The method of claim 1, wherein calculating the resting microvascular resistance at the termination of each of the plurality of branches using the patient-specific anatomical measurements and the non-invasive clinical measurements of the patient at rest comprises:
   calculating the mean arterial pressure (MAP) as a function of the measured heart rate, the measured systolic blood pressure, and a measured diastolic blood pressure of the patient;
   calculating a resting myocardial perfusion as a function of a rate-pressure product that is a product of the measured heart rate and the measured systolic blood pressure of the patient;
   calculating a total resting coronary flow as a function of the calculated resting myocardial perfusion and a mass of a left ventricle of the patient; and
   calculating the resting microvascular resistance at the termination of each of the plurality of branches as a function of the MAP and the total resting coronary flow.

13. The method of claim 12, wherein the mass of the left ventricle is estimated from the medical image data of the patient.

14. The method of claim 1, wherein calculating fractional flow reserve (FFR) of the at least one stenosis region using the simulated hyperemic blood flow and pressure comprises:
   calculating the FFR of the at least one stenosis region as a ratio of a mean simulated hyperemic pressure distal to the at least one stenosis and a mean simulated hyperemic aortic pressure over a cardiac cycle.

15. An apparatus for non-invasive assessment of coronary artery stenosis, comprising:
   a processor; and
   a memory storing computer program instructions, which when executed by the processor cause the processor to perform operations comprising:
   extracting patient-specific anatomical measurements of the coronary arteries from medical image data of a patient acquired during a rest state;
   automatically detecting at least one stenosis region in at least one coronary artery from the medical image data;
   calculating patient-specific rest state boundary conditions of a model of coronary circulation representing the coronary arteries using the patient-specific anatomical measurements and non-invasive clinical measurements of the patient at rest, wherein calculating the patient-specific rest state boundary conditions comprises calculating a resting microvascular resistance at a termination of each of a plurality of branches of the coronary arteries using the patient-specific anatomical measurements and the non-invasive clinical measurements of the patient at rest;
   calculating patient-specific hyperemic boundary conditions of the model of coronary circulation using the rest boundary conditions and a model for simulated hyperemia, wherein the model for simulated hyperemia simulates hyperemia in the patient by changing only the resting microvascular resistance at a termination of each of a plurality of branches of the coronary arteries to a hyperemic microvascular resistance calculated as a function of the resting microvascular resistance at the termination of each of the plurality of branches without changing blood pressure or heart rate boundary conditions, and wherein calculating the patient-specific hyperemic boundary conditions comprises calculating the hyperemic microvascular resistance at the termination of each of the plurality of branches using the calculated resting microvascular resistance by:
      calculating a resting average peak velocity as a function of a measured heart rate and a measured systolic blood pressure of the patient,
      calculating a coronary flow velocity reserve (CFVR) value for each branch of the coronary arteries as a function of the resting average peak velocity and an age of the patient,
      calculating a patient-specific total coronary resistance index (TCRI) as a function of the CFVR value and an estimated resting mean arterial pressure (MAP), and
      calculating the hyperemic microvascular resistance at the termination of each of the plurality of branches as a function of the calculated resting microvascular resistance and the patient-specific TCRI;
   simulating hyperemic blood flow and pressure across the at least one automatically detected stenosis region of the at least one coronary artery using the model of coronary circulation and the patient-specific hyperemic boundary conditions, wherein the model of coronary circulation comprises a reduced order stenosis pressure drop model representing the at least one stenosis region and the reduced order stenosis pressure drop model calculates a pressure drop across the at least one stenosis region as a sum of a viscous term, a turbulent term, and an inertance term:

$$\Delta P_s = \frac{\mu K_v}{2\pi r_0^3} q + \frac{\rho K_t}{2A_0^2}\left(\frac{A_0}{A_s} - 1\right)^2 |q|q + \frac{\rho K_u L_s}{A_0} \frac{\partial q}{\partial t},$$

where $\mu$ is blood viscosity, $L_s$ is a length of the at least one stenosis region, q is a flow rate, $A_s$ is a cross-sectional area of the at least one stenosis region, $A_0$ is a cross-sectional area of a non-stenosis region in the at least one coronary artery, $\rho$ is a blood density, $r_0$ is a radius of the non-stenosis region in the at least one coronary artery, and $K_v$, $K_t$ and $K_u$ are viscous, turbulent, and inertance coefficients, respectively; and
   calculating fractional flow reserve (FFR) of the at least one stenosis region using the simulated hyperemic blood flow and pressure.

16. The apparatus of claim 15, wherein the coronary circulation model comprises one-dimensional computational models representing the coronary arteries and aorta of the patient.

17. The apparatus of claim 15, wherein calculating the resting microvascular resistance at the termination of each of the plurality of branches using the patient-specific anatomical measurements and the non-invasive clinical measurements of the patient at rest comprises:
  calculating the mean arterial pressure (MAP) as a function of the measured heart rate, the measured systolic blood pressure, and a measured diastolic blood pressure of the patient;
  calculating a resting myocardial perfusion as a function of a rate-pressure product that is a product of the measured heart rate and the measured systolic blood pressure of the patient;
  calculating a total resting coronary flow as a function of the calculated resting myocardial perfusion and a mass of a left ventricle of the patient; and
  calculating the resting microvascular resistance at the termination of each of the plurality of branches as a function of the MAP and the total resting coronary flow.

18. A non-transitory computer readable medium storing computer program instructions for non-invasive assessment of coronary artery stenosis, the computer program instructions when executed by a processor cause the processor to perform operations comprising:
  extracting patient-specific anatomical measurements of the coronary arteries from medical image data of a patient acquired during a rest state;
  automatically detecting at least one stenosis region in at least one coronary artery from the medical image data;
  calculating patient-specific rest state boundary conditions of a model of coronary circulation representing the coronary arteries using the patient-specific anatomical measurements and non-invasive clinical measurements of the patient at rest, wherein calculating the patient-specific rest state boundary conditions comprises calculating a resting microvascular resistance at a termination of each of a plurality of branches of the coronary arteries using the patient-specific anatomical measurements and the non-invasive clinical measurements of the patient at rest;
  calculating patient-specific hyperemic boundary conditions of the model of coronary circulation using the rest boundary conditions and a model for simulated hyperemia, wherein the model for simulated hyperemia simulates hyperemia in the patient by changing only the resting microvascular resistance at a termination of each of a plurality of branches of the coronary arteries to a hyperemic microvascular resistance calculated as a function of the resting microvascular resistance at the termination of each of the plurality of branches without changing blood pressure or heart rate boundary conditions, and wherein calculating the patient-specific hyperemic boundary conditions comprises calculating the hyperemic microvascular resistance at the termination of each of the plurality of branches using the calculated resting microvascular resistance by:
    calculating a resting average peak velocity as a function of a measured heart rate and a measured systolic blood pressure of the patient,
    calculating a coronary flow velocity reserve (CFVR) value for each branch of the coronary arteries as a function of the resting average peak velocity and an age of the patient,
    calculating a patient-specific total coronary resistance index (TCRI) as a function of the CFVR value and an estimated resting mean arterial pressure (MAP), and
    calculating the hyperemic microvascular resistance at the termination of each of the plurality of branches as a function of the calculated resting microvascular resistance and the patient-specific TCRI;
  simulating hyperemic blood flow and pressure across the at least one automatically detected stenosis region of the at least one coronary artery using the model of coronary circulation and the patient-specific hyperemic boundary conditions, wherein the model of coronary circulation comprises a reduced order stenosis pressure drop model representing the at least one stenosis region and the reduced order stenosis pressure drop model calculates a pressure drop across the at least one stenosis region as a sum of a viscous term, a turbulent term, and an inertance term:

$$\Delta P_s = \frac{\mu K_v}{2\pi r_0^3} q + \frac{\rho K_t}{2 A_0^2}\left(\frac{A_0}{A_s} - 1\right)^2 |q|q + \frac{\rho K_u L_s}{A_0}\frac{\partial q}{\partial t},$$

where $\mu$ is blood viscosity, $L_s$ is a length of the at least one stenosis region, q is a flow rate, $A_s$ is a cross-sectional area of the at least one stenosis region, $A_0$ is a cross-sectional area of a non-stenosis region in the at least one coronary artery, $\rho$ is a blood density, $r_0$ is a radius of the non-stenosis region in the at least one coronary artery, and $K_v$, $K_t$ and $K_u$ are viscous, turbulent, and inertance coefficients, respectively; and
  calculating fractional flow reserve (FFR) of the at least one stenosis region using the simulated hyperemic blood flow and pressure.

19. The non-transitory computer readable medium of claim 18, wherein the coronary circulation model comprises one-dimensional computational models representing the coronary arteries and aorta of the patient.

20. The non-transitory computer readable medium of claim 18, wherein calculating the resting microvascular resistance at the termination of each of the plurality of branches based on the patient-specific anatomical measurements and the non-invasive clinical measurements of the patient at rest comprises:
  calculating the mean arterial pressure (MAP) as a function of the measured heart rate, the measured systolic blood pressure, and a measured diastolic blood pressure of the patient;
  calculating a resting myocardial perfusion as a function of a rate-pressure product that is a product of the measured heart rate and the measured systolic blood pressure of the patient;
  calculating a total resting coronary flow as a function of the calculated resting myocardial perfusion and a mass of a left ventricle of the patient; and
  calculating the resting microvascular resistance at the termination of each of the plurality of branches as a function of the MAP and the total resting coronary flow.

21. The non-transitory computer readable medium of claim 18, wherein calculating fractional flow reserve (FFR) of the at least one stenosis region using the simulated hyperemic blood flow and pressure comprises:
  calculating the FFR of the at least one stenosis region as a ratio of a mean simulated hyperemic pressure distal to the at least one stenosis and a mean simulated hyperemic aortic pressure over a cardiac cycle.

* * * * *